United States Patent
Gonzalez et al.

(10) Patent No.: US 10,876,728 B2
(45) Date of Patent: Dec. 29, 2020

(54) PROCESS FOR MANAGING PHOTOBIOREACTOR EXHAUST

(71) Applicant: POND TECHNOLOGIES INC., Markham (CA)

(72) Inventors: Jaime A. Gonzalez, Markham (CA); Steven C. Martin, Toronto (CA); Max Kolesnik, Toronto (CA)

(73) Assignee: Pond Technologies Inc., Markham (CA)

( * ) Notice: Subject to any disclaimer, the term of this patent is extended or adjusted under 35 U.S.C. 154(b) by 0 days.

(21) Appl. No.: 15/347,293

(22) Filed: Nov. 9, 2016

(65) Prior Publication Data

US 2017/0248309 A1   Aug. 31, 2017

Related U.S. Application Data

(63) Continuation of application No. 13/826,461, filed on Mar. 14, 2013, now abandoned.

(60) Provisional application No. 61/753,711, filed on Jan. 17, 2013, provisional application No. 61/759,656, filed on Feb. 1, 2013.

(51) Int. Cl.
| | |
|---|---|
| *B01D 53/84* | (2006.01) |
| *C12N 1/12* | (2006.01) |
| *F23G 7/06* | (2006.01) |
| *B01D 53/62* | (2006.01) |

(52) U.S. Cl.
CPC .............. *F23G 7/06* (2013.01); *B01D 53/62* (2013.01); *B01D 53/84* (2013.01); *C12N 1/12* (2013.01); *F23G 7/065* (2013.01); *B01D 2251/95* (2013.01); *B01D 2257/302* (2013.01); *B01D 2257/404* (2013.01); *B01D 2257/406* (2013.01); *B01D 2257/504* (2013.01); *B01D 2258/0283* (2013.01); *B01D 2259/802* (2013.01); *F23G 2206/20* (2013.01); *Y02A 50/20* (2018.01); *Y02C 20/40* (2020.08); *Y02E 50/30* (2013.01)

(58) Field of Classification Search
None
See application file for complete search history.

(56) References Cited

U.S. PATENT DOCUMENTS

| | | | |
|---|---|---|---|
| 4,253,271 A | 3/1981 | Raymond | .................... 47/1.4 |
| 2005/0252215 A1 | 11/2005 | Beaumont | |
| 2009/0130704 A1 | 5/2009 | Gyure | |
| 2010/0233787 A1 | 9/2010 | Katchanov | |
| 2013/0224841 A1 | 8/2013 | Bliss | |

FOREIGN PATENT DOCUMENTS

| | | |
|---|---|---|
| CA | 2 738 418 | 11/2011 |
| DE | 4212334 C1 | 6/1993 |
| WO | WO 2007/047805 | 4/2007 |
| WO | 2009034365 A1 | 3/2009 |
| WO | 2009156474 A1 | 12/2009 |
| WO | WO 2010/010554 | 1/2010 |
| WO | WO 2010/123943 | 10/2010 |
| WO | 20110143749 A2 | 11/2011 |
| WO | WO/2012/145835 | 11/2012 |

OTHER PUBLICATIONS

Extended European Search Report for EP11782806.1 dated Aug. 1, 2014.
Extended European Search Report for EP11858246.9 dated Sep. 17, 2014.
Kunjapur et al., "Photobioreactor Design for Commercial Biofuel Production from Microalgae," Ind. Eng. Chem. Res. 49:3516-3526, 2010.
Chinese Office Action issued in Chinese Application No. 201480016474. 3, dated May 2, 2018.
EPO, Extended European Search Report for EP Application No. 147404291 dated Nov. 24, 2016.
USPTO, Office Action for U.S. Appl. No. 13/826,461 dated May 9, 2016.
Search Report and Written Opinion in International Application No. PCT/CA2014/000034 dated Apr. 28, 2014.
Office Action; CA Application No. 2,898,315 dated Oct. 22, 2019.
Office Action; IN Application No. 6307/DELNP/2015 dated Nov. 29, 2019.
Office Action; CN Application No. 2014800164743 dated Mar. 31, 2020 (original Chinese).
Office Action; CN Application No. 2014800164743 dated Mar. 31, 2020 (translated English).

*Primary Examiner* — Allison M Fox
(74) *Attorney, Agent, or Firm* — Ridout and Maybee LLP

(57) ABSTRACT

There is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone. The process includes supplying at least a fraction of gaseous exhaust material, being discharged from an industrial process, to the reaction zone, exposing the reaction mixture to photosynthetically active light radiation and effecting growth of the phototrophic biomass in the reaction zone, wherein the effected growth includes growth effected by photosynthesis, and modulating distribution of a molar rate of supply of carbon dioxide, being exhausted from the reaction zone, as between a smokestack and at least another point of discharge.

8 Claims, 5 Drawing Sheets

US 10,876,728 B2

PROCESS FOR MANAGING PHOTOBIOREACTOR EXHAUST

CROSS-REFERENCE TO RELATED APPLICATIONS

This application is a continuation of U.S. application Ser. No. 13/826,461, filed Mar. 14, 2013, which claims priority to U.S. Provisional Application No. 61/753,711 filed Jan. 17, 2013, and U.S. Provisional Application No. 61/759,656 filed Feb. 1, 2013. The entire contents of each of the above-referenced disclosures is specifically incorporated herein by reference without disclaimer.

FIELD

The present disclosure relates to a process for growing biomass.

BACKGROUND

The cultivation of phototrophic organisms has been widely practised for purposes of producing a fuel source. Exhaust gases from industrial processes have also been used to promote the growth of phototrophic organisms by supplying carbon dioxide for consumption by phototrophic organisms during photosynthesis. By providing exhaust gases for such purpose, environmental impact is reduced and, in parallel a potentially useful fuel source is produced. Challenges remain, however, to render this approach more economically attractive for incorporation within existing facilities.

SUMMARY

In one aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone. The process includes supplying at least a fraction of gaseous exhaust material, being discharged from an industrial process, to the reaction zone, exposing the reaction mixture to photosynthetically active light radiation and effecting growth of the phototrophic biomass in the reaction zone, wherein the effected growth includes growth effected by photosynthesis, and modulating distribution of a molar rate of supply of carbon dioxide, being exhausted from the reaction zone, as between a smokestack and at least another point of discharge.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone. The process includes supplying at least a fraction of gaseous exhaust material, being discharged from an industrial process, to the reaction zone, exposing the reaction mixture to photosynthetically active light radiation and effecting growth of the phototrophic biomass in the reaction zone, wherein the effected growth includes growth effected by photosynthesis, discharging a gaseous exhaust from the reaction zone, separating at least an oxygen-rich product from the gaseous exhaust that is discharged from the reaction zone, and contacting the oxygen-rich product with a fuel to effect combustion.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone. The process includes supplying at least a fraction of gaseous exhaust material, being discharged from an industrial process, to the reaction zone, exposing the reaction mixture to photosynthetically active light radiation and effecting growth of the phototrophic biomass in the reaction zone, wherein the effected growth includes growth effected by photosynthesis, discharging gaseous exhaust from the reaction zone, separating at least an oxygen-depleted product from the gaseous exhaust that is discharged from the reaction zone, and supplying the oxygen-depleted product to the reaction zone.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone. The process includes supplying at least a fraction of gaseous exhaust material, being discharged from an industrial process, to the reaction zone, exposing the reaction mixture to photosynthetically active light radiation and effecting growth of the phototrophic biomass in the reaction zone, wherein the effected growth includes growth effected by photosynthesis, discharging gaseous exhaust from the reaction zone, and recycling at least a fraction of the discharging gaseous exhaust to the reaction zone.

BRIEF DESCRIPTION OF DRAWINGS

The process of the preferred embodiments of the invention will now be described with the following accompanying drawing.

DETAILED DESCRIPTION

Reference throughout the specification to "some embodiments" means that a particular feature, structure, or characteristic described in connection with some embodiments are not necessarily referring to the same embodiments. Furthermore, the particular features, structure, or characteristics may be combined in any suitable manner with one another.

Figure 1:
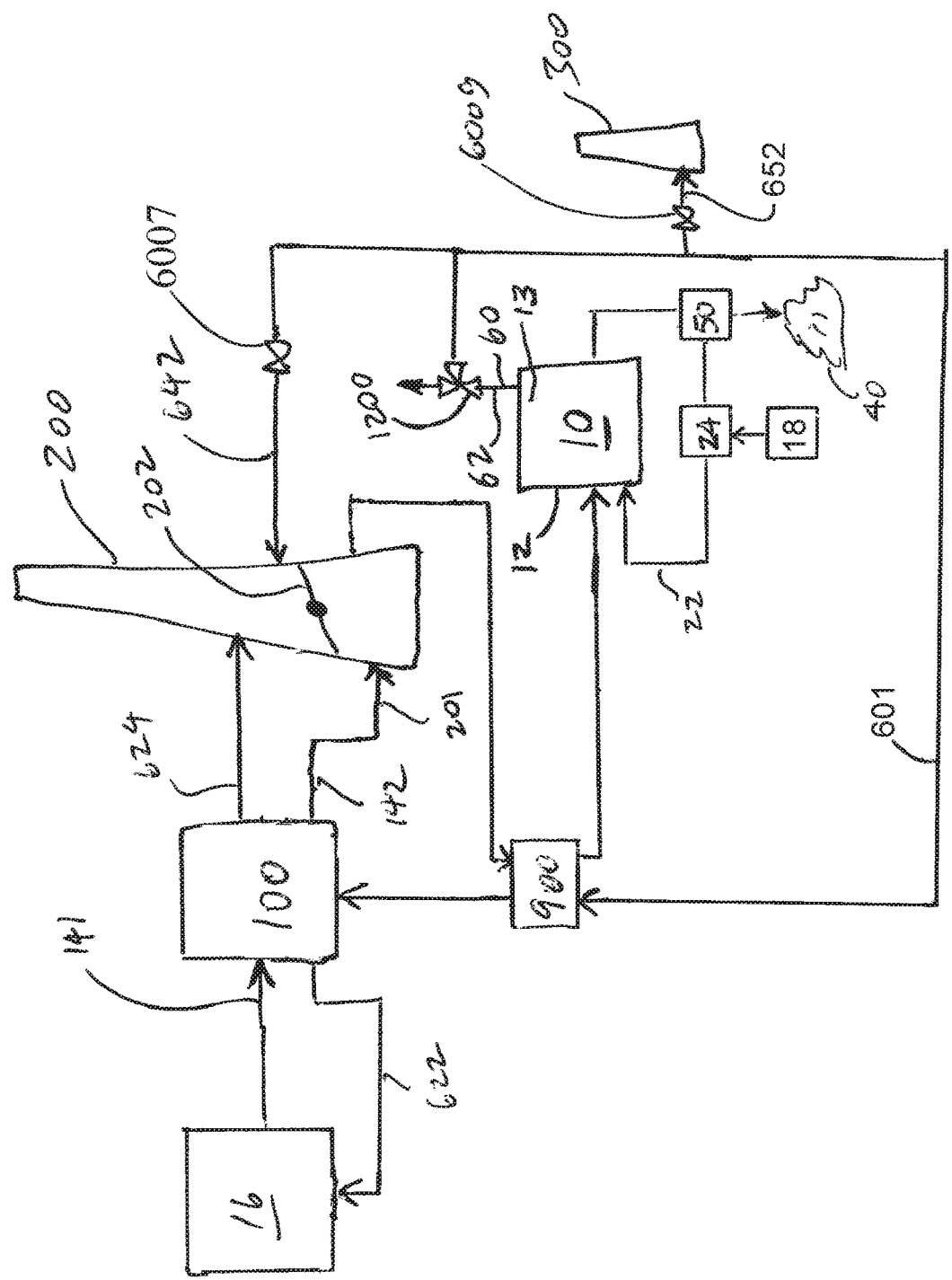
FIG. 1 is a process flow diagram of an embodiment of a system embodying the process.

Referring to FIG. 1, a system is provided for facilitating a process of growing a phototrophic biomass within a reaction zone 10 of a photobioreactor 12.

The reaction zone 10 includes a reaction mixture that is operative for effecting photosynthesis upon exposure to photosynthetically active light radiation. The reaction mixture includes phototrophic biomass, carbon dioxide, and water. In some embodiments, the reaction zone includes phototrophic biomass and carbon dioxide disposed in an aqueous medium. Within the reaction zone 10, the phototrophic biomass is disposed in mass transfer communication with both of carbon dioxide and water.

"Phototrophic organism" is an organism capable of phototrophic growth in the aqueous medium upon receiving light energy, such as plant cells and micro-organisms. The phototrophic organism is unicellular or multicellular. In some embodiments, for example, the phototrophic organism is an organism which has been modified artificially or by gene manipulation. In some embodiments, for example, the phototrophic organism is an algae. In some embodiments, for example, the algae is microalgae.

"Phototrophic biomass" is at least one phototrophic organism. In some embodiments, for example, the phototrophic biomass includes more than one species of phototrophic organisms.

"Reaction zone 10" defines a space within which the growing of the phototrophic biomass is effected. In some embodiments, for example, pressure within the reaction zone is atmospheric pressure.

"Photobioreactor 12" is any structure, arrangement, land formation or area that provides a suitable environment for the growth of phototrophic biomass. Examples of specific structures which can be used is a photobioreactor 12 by providing space for growth of phototrophic biomass using light energy include, without limitation, tanks, ponds, troughs, ditches, pools, pipes, tubes, canals, and channels. Such photobioreactors may be either open, closed, partially closed, covered, or partially covered. In some embodiments, for example, the photobioreactor 12 is a pond, and the pond is open, in which case the pond is susceptible to uncontrolled receiving of materials and light energy from the immediate environments. In other embodiments, for example, the photobioreactor 12 is a covered pond or a partially covered pond, in which case the receiving of materials from the immediate environment is at least partially interfered with. The photobioreactor 12 includes the reaction zone 10 which includes the reaction mixture. In some embodiments, the photobioreactor 12 is configured to receive a supply of phototrophic reagents (and, in some of these embodiments, optionally, supplemental nutrients), and is also configured to effect discharge of phototrophic biomass which is grown within the reaction zone 10. In this respect, in some embodiments, the photobioreactor 12 includes one or more inlets for receiving the supply of phototrophic reagents and supplemental nutrients, and also includes one or more outlets for effecting the recovery or harvesting of biomass which is grown within the reaction zone 10. In some embodiments, for example, one or more of the inlets are configured to be temporarily sealed for periodic or intermittent time intervals. In some embodiments, for example, one or more of the outlets are configured to be temporarily sealed or substantially sealed for periodic or intermittent time intervals. The photobioreactor 12 is configured to contain the reaction mixture which is operative for effecting photosynthesis upon exposure to photosynthetically active light radiation. The photobioreactor 12 is also configured so as to establish photosynthetically active light radiation (for example, a light of a wavelength between about 400-700 nm, which can be emitted by the sun or another light source) within the photobioreactor 12 for exposing the phototrophic biomass.

The exposing of the reaction mixture to the photosynthetically active light radiation effects photosynthesis and growth of the phototrophic biomass. In some embodiments, for example, the established light radiation is provided by an artificial light source 14 disposed within the photobioreactor 12. For example, suitable artificial lights sources include submersible fiber optics or light guides, light-emitting diodes ("LEDs"), LED strips and fluorescent lights. Any LED strips known in the art can be adapted for use in the photobioreactor 12. In the case of the submersible LEDs, in some embodiments, for example, energy sources include alternative energy sources, such as wind, photovoltaic cells, fuel cells, etc. to supply electricity to the LEDs. Fluorescent lights, external or internal to the photobioreactor 12, can be used as a back-up system. In some embodiments, for example, the established light is derived from a natural light source 16 which has been transmitted from externally of the photobioreactor 12 and through a transmission component. In some embodiments, for example, the transmission component is a portion of a containment structure of the photobioreactor 12 which is at least partially transparent to the photosynthetically active light radiation, and which is configured to provide for transmission of such light to the reaction zone 10 for receiving by the phototrophic biomass. In some embodiments, for example, natural light is received by a solar collector, filtered with selective wavelength filters, and then transmitted to the reaction zone 10 with fiber optic material or with a light guide. In some embodiments, for example, both natural and artificial lights sources are provided for effecting establishment of the photosyntetically active light radiation within the photobioreactor 12.

"Aqueous medium" is an environment that includes water. In some embodiments, for example, the aqueous medium also includes sufficient nutrients to facilitate viability and growth of the phototrophic biomass. In some embodiments, for example, supplemental nutrients may be included such as one of, or both of, $NO_X$ and $SO_X$. Suitable aqueous media are discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each of which is incorporated herein by reference). A suitable supplemental nutrient composition, known as "Bold's Basal Medium", is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae from Enchanted Rock and related algal species*, Univ. Texas Publ. 6318: 1-95 and Stein, J. (ED.) *Handbook of Phycological Processs, Culture processs and growth measurements*, Cambridge University Press, pp. 7-24).

"Headspace" is that space within the photobioreactor 12 that is above the aqueous medium within the photobioreactor 12.

Carbon dioxide is supplied to the reaction zone 10 of the photobioreactor 12 for effecting the growth of the phototrophic biomass. In some embodiments, for example, the carbon dioxide being supplied to the photobioreactor is supplied by at least a fraction of the carbon dioxide-comprising exhaust material 14 being discharged by a carbon dioxide-comprising gaseous exhaust material producing process 16. The at least a fraction of the carbon dioxide-comprising exhaust material 14, that is being supplied to the photobioreactor 12, defines the photobioreactor supply 122.

In some embodiments, for example, the carbon dioxide-comprising gaseous exhaust material 14 includes a carbon dioxide concentration of at least two (2) volume % based on the total volume of the carbon dioxide-comprising gaseous exhaust material 14. In some embodiments, for example, the carbon dioxide-comprising gaseous exhaust material 14 includes a carbon dioxide concentration of at least four (4) volume % based on the total volume of the carbon dioxide-comprising gaseous exhaust material 14. In some embodiments, for example, the gaseous exhaust material reaction 14 also includes one or more of $N_2$, $CO_2$, $H_2O$, $O_2$, $NO_x$, $SO_x$, CO, volatile organic compounds (such as those from unconsumed fuels) heavy metals, particulate matter, and ash. In some embodiments, for example, the carbon dioxide-comprising gaseous exhaust material 14 includes 30 to 60 volume % $N_2$, 5 to 25 volume % $O_2$, 2 to 50 volume % $CO_2$, and 0 to 30 volume % $H_2O$, based on the total volume of the carbon dioxide-comprising gaseous exhaust material 14. Other compounds may also be present, but usually in trace amounts (cumulatively, usually less than five (5) volume % based on the total volume of the carbon dioxide-comprising gaseous exhaust material 14).

In some embodiments, for example, the carbon dioxide-comprising gaseous exhaust material 14 includes one or more other materials, other than carbon dioxide, that are beneficial to the growth of the phototrophic biomass within the reaction zone 10. Materials within the gaseous exhaust material which are beneficial to the growth of the phototrophic biomass within the reaction zone 10 include $SO_x$, $NO_x$, and $NH_3$.

The carbon dioxide-comprising gaseous exhaust material producing process 16 includes any process which effects production and discharge of the carbon dioxide-comprising gaseous exhaust material 14. In some embodiments, for example, the carbon dioxide-comprising gaseous exhaust material producing process 16 is a combustion process. In some embodiments, for example, the combustion process is effected in a combustion facility. In some of these embodiments, for example, the combustion process effects combustion of a fossil fuel, such as coal, oil, or natural gas. For example, the combustion facility is any one of a fossil fuel-fired power plant, an industrial incineration facility, an industrial furnace, an industrial heater, or an internal combustion engine. In some embodiments, for example, the combustion facility is a cement kiln.

In some embodiments, for example, a supplemental nutrient supply 18 is supplied to the reaction zone 10 of the photobioreactor 12. In some embodiments, for example, the supplemental nutrient supply 18 is effected by a pump, such as a dosing pump. In other embodiments, for example, the supplemental nutrient supply 18 is supplied manually to the reaction zone 10. Nutrients within the reaction zone 10 are processed or consumed by the phototrophic biomass, and it is desirable, in some circumstances, to replenish the processed or consumed nutrients. A suitable nutrient composition is "Bold's Basal Medium", and this is described in Bold, H. C. 1949, *The morphology of Chlamydomonas chlamydogama sp. nov. Bull. Torrey Bot. Club.* 76: 101-8 (see also Bischoff. H. W. and Bold, H. C. 1963. *Phycological Studies IV. Some soil algae from Enchanted Rock and related algal species*, Univ. Texas Pub 6318: 1-95, and Stein, J. (ED.) *Handbook of Phycological Processs, Culture processs and growth measurements*, Cambridge University Press, pp. 7-24). The supplemental nutrient supply 18 is supplied for supplementing the nutrients provided within the reaction zone, such as "Bold's Basal Medium", or one or more dissolved components thereof. In this respect, in some embodiments, for example, the supplemental nutrient supply 18 includes "Bold's Basal Medium". In some embodiments for example, the supplemental nutrient supply 18 includes one or more dissolved components of "Bold's Basal Medium", such as $NaNO_3$, $CaCl_2$, $MgSO_4$, $KH_2PO_4$, NaCl, or other ones of its constituent dissolved components.

In some embodiments, for example, the rate of supply of the supplemental nutrient supply 18 to the reaction zone 10 is controlled to align with a desired rate of growth of the phototrophic biomass in the reaction zone 10. In some embodiments, for example, regulation of nutrient addition is monitored by measuring any combination of pH, $NO_3$ concentration, and conductivity in the reaction zone 10.

In some embodiments, for example, a supply of the supplemental aqueous material supply 20 is effected to the reaction zone 10 of the photobioreactor 12, so as to replenish water within the reaction zone 10 of the photobioreactor 12. In some embodiments, for example, and as further described below, the supplemental aqueous material supply 20 effects the discharge of product from the photobioreactor 12 by displacement. For example, the supplemental aqueous material supply 20 effects the discharge of product from the photobioreactor 12 as an overflow.

In some embodiments, for example, the supplemental aqueous material is water or substantially water. In some embodiments, for example, the supplemental aqueous material supply 20 includes aqueous material that has been separated from a discharged phototrophic biomass-comprising product 32 by a separator 50 (such as a centrifugal separator). In some embodiments, for example, the supplemental aqueous material supply 20 is derived from an independent source (ie. a source other than the process), such as a municipal water supply.

In some embodiments, for example, the supplemental aqueous material supply 20 is supplied from a container that has collected aqueous material recovered from discharges from the process, such as aqueous material that has been separated from a discharged phototrophic biomass-comprising product.

In some embodiments, for example, the supplemental nutrient supply 18 is mixed with the supplemental aqueous material 20 in a mixing tank 24 to provide a nutrient-enriched supplemental aqueous material supply 22, and the nutrient-enriched supplemental aqueous material supply 22 is supplied to the reaction zone 10. In some embodiments, for example, the supplemental nutrient supply 18 is mixed with the supplemental aqueous material 20 within the container which has collected the discharged aqueous material. In some embodiments, for example, the supply of the nutrient-enriched supplemental aqueous material supply 18 is effected by a pump.

The reaction mixture disposed in the reaction zone 10 is exposed to photosynthetically active light radiation so as to effect photosynthesis. The photosynthesis effects growth of the phototrophic biomass.

In some embodiments, for example, light radiation is supplied to the reaction zone 10 for effecting the photosynthesis.

In some embodiments, for example, the light radiation is characterized by a wavelength of between 400-700 nm. In some embodiments, for example, the light radiation is in the form of natural sunlight. In some embodiments, for example, the light radiation is provided by an artificial light source. In some embodiments, for example, light radiation includes natural sunlight and artificial light.

In some embodiments, for example, the intensity of the supplied light radiation is controlled so as to align with the desired growth rate of the phototrophic biomass in the reaction zone 10. In some embodiments, regulation of the intensity of the provided light is based on measurements of the growth rate of the phototrophic biomass in the reaction zone 10. In some embodiments, regulation of the intensity of the provided light is based on the molar rate of supply of carbon dioxide to the reaction zone feed material 80.

In some embodiments, for example, the light radiation is supplied at pre-determined wavelengths, depending on the conditions of the reaction zone 10. Having said that, generally, the light is provided in a blue light source to red light source ratio of 1:4. This ratio varies depending on the phototrophic organism being used. As well, this ratio may vary when attempting to simulate daily cycles. For example, to simulate dawn or dusk, more red light is provided, and to simulate mid-day condition, more blue light is provided. Further, this ratio may be varied to simulate artificial recovery cycles by providing more blue light.

It has been found that blue light stimulates algae cells to rebuild internal structures that may become damaged after a period of significant growth, while red light promotes algae growth. Also, it has been found that omitting green light from the spectrum allows algae to continue growing in the reaction zone 10 even beyond what has previously been identified as its "saturation point" in water, so long as sufficient carbon dioxide and, in some embodiments, other nutrients, are supplied.

With respect to artificial light sources, for example, suitable artificial light source 14 include submersible fiber optics, light-emitting diodes, LED strips and fluorescent lights. Any LED strips known in the art can be adapted for use in the process. In the case of the submersible LEDs, the design includes the use of solar powered batteries to supply the electricity. In the case of the submersible LEDs, in some embodiments, for example, energy sources include alternative energy sources, such as wind, photovoltaic cells, fuel cells, etc. to supply electricity to the LEDs.

With respect to those embodiments where the reaction zone 10 is disposed in a photobioreactor 12 which includes a tank, in some of these embodiments, for example, the light energy is provided from a combination of sources, as follows. Natural light source in the form of solar light is captured though solar collectors and filtered with custom mirrors that effect the provision of light of desired wavelengths to the reaction zone 10. The filtered light from the solar collectors is then transmitted through light guides or fiber optic materials into the photobioreactor 12, where it becomes dispersed within the reaction zone 10. In some embodiments, in addition to solar light, the light tubes in the photobioreactor 12 contains high power LED arrays that can provide light at specific wavelengths to either complement solar light, as necessary, or to provide all of the necessary light to the reaction zone 10 during periods of darkness (for example, at night). In some embodiments, with respect to the light guides, for example, a transparent heat transfer medium (such as a glycol solution) is circulated through light guides within the photobioreactor 12 so as to regulate the temperature in the light guides and, in some circumstances, provide for the controlled dissipation of heat from the light guides and into the reaction zone 10. In some embodiments, for example, the LED power requirements can be predicted and, therefore, controlled, based on trends observed with respect to the carbon dioxide-comprising gaseous exhaust material 14, as these observed trends assist in predicting future growth rate of the phototrophic biomass.

In some embodiments, the exposing of the reaction mixture to photosynthetically active light radiation is effected while the supplying of the carbon dioxide to the reaction zone 10 is being effected.

In some embodiments, for example, the growth rate of the phototrophic biomass is dictated by the available carbon dioxide within the reaction zone 10. In turn, this defines the nutrient, water, and light intensity requirements to maximize phototrophic biomass growth rate. In some embodiments, for example, a controller, e.g. a computer-implemented system, is provided to be used to monitor and control the operation of the various components of the process disclosed herein, including lights, valves, sensors, blowers, fans, dampers, pumps, etc.

In some embodiments, for example, reaction zone product 30 is discharged from the reaction zone 10. The reaction zone product 30 includes phototrophic biomass-comprising product 32. In some embodiments, for example, the phototrophic biomass-comprising product 32 includes at least a fraction of the contents of the reaction zone 10. In this respect, the discharge of the reaction zone product 30 effects harvesting of the phototrophic biomass 40.

In some embodiments, for example, the harvesting of the phototrophic biomass is effected by discharging the phototrophic biomass 32 from the reaction zone 10.

In some embodiments, for example, the discharging of the phototrophic biomass 32 from the reaction zone 10 is effected by displacement. In some of these embodiments, for example, the displacement is effected by supplying supplemental aqueous material supply 20 to the reaction zone 10. In some of these embodiments, for example, the displacement is an overflow. In some embodiments, for example, the discharging of the phototrophic biomass 32 from the reaction zone 10 is effected by gravity. In some embodiments, for example, the discharging of the phototrophic biomass 32 from the reaction zone 10 is effected by a prime mover that is fluidly coupled to the reaction zone 10.

In some embodiments, for example, the at least a fraction of carbon dioxide-comprising gaseous exhaust material 14 is passed through the reaction zone 10 for effecting the photosynthesis such that the carbon dioxide-comprising gaseous exhaust material 14 becomes depleted in carbon dioxide, and such that production of a gaseous photobioreactor exhaust 60, including photobioreactor-exhausted carbon dioxide, is effected and exhausted into the headspace 13. In some embodiments, for example, the carbon dioxide concentration within the gaseous photobioreactor exhaust 60 is less than the carbon dioxide concentration within the carbon dioxide-comprising gaseous exhaust material 14.

In some embodiments, for example, at least a fraction of the carbon dioxide-comprising gaseous exhaust material 14 is supplied to a gas treatment process 100, as pre-treated gaseous exhaust material 141 to generate a treated gaseous exhaust material 142. The gas treatment process 100 includes one or more separate unit operations for effecting separation of at least a fraction of the pre-treated gaseous exhaust material 141 to yield treated gaseous exhaust material 142. Exemplary unit operations include bag houses, $NO_X$ filters, $SO_X$ filters, electrostatic fluidized beds, membrane separation unit operations (such as for effecting separation of gaseous diatomic oxygen from the pre-treated material 141).

In some embodiments, for example, at least a fraction of the treated material 142 is supplied as the photobioreactor supply 122.

In some embodiments, for example, at least a fraction of the treated material 142 is supplied to the smokestack 200.

In some embodiments, for example, a fraction of the treated material 142 is supplied to the smokestack 200 as a smokestack supply 201, while another fraction of the treated material 142 is supplied to the photobioreactor 12 as the photobioreactor supply 122. In some embodiments, for example, the fraction supplied as the smokestack supply 201, and the fraction supplied as the photobioreactor supply 122, is determined by a damper or stack cap 202 within the smokestack. The damper or stack cap 202 is biased (such as by spring forces) to seal fluid communication between the treated material 142 and the smokestack such that all of the treated material 142 is supplied to the reaction zone 10 of the photobioreactor 12. The damper or stack cap 202 is configured to become disposed so as to effect fluid communication between the treated material and the smokestack when the fluid pressure of the treated material is sufficient to overcome the forces biasing the damper or stack cap to be disposed in a condition to effect the sealing of the fluid communication, and thereby effect opening of the fluid communication, thereby diverting a fraction of the treated material to the smokestack 200

In some embodiments, for example, there is no gas treatment process 100, and at least a fraction of the exhaust material 14 is supplied directly to the smokestack 200 as a smokestack supply. In some of these embodiments, for example, a fraction of the exhaust material 14 is supplied to the smokestack 200 as the smokestack supply 201, while another fraction of the exhaust material 14 is supplied to the photobioreactor 12 as the photobioreactor supply 122. In some embodiments, for example, the fraction supplied as the smokestack supply 201, and the fraction supplied as the photobioreactor supply 122, is determined by a damper or stack cap 202 within the smokestack, as described above.

The photobioreactor exhaust 60 is discharged from the photobioreactor 12.

The rate of discharging of the exhaust 60 is modulated as between a local discharge 61 and a further processing discharge 62 by a valve 1200, based on sensed concentrations of various gases, such as carbon dioxide, diatomic oxygen, $NO_X$, and $SO_X$. It is desirable for exhaust 60 having excessive carbon dioxide, $NO_X$, or $SO_X$ concentrations not to be exhausted, locally, at ground level, and to direct such exhaust 60 for recycling within the process, or to the smokestack 200, or to a cold stack 300. Depending on the configuration of the system, sensed gaseous diatomic oxygen may determine whether to recycle the exhaust (for example, if gaseous diatomic oxygen concentration is below a minimum threshold for effecting combustion of fuel) or to conduct the exhaust to the process 16 (for example, if gaseous diatomic oxygen concentration is sufficient for effecting combustion of fuel), or a combination of both. Sensing of excessive concentrations of one or more of these gases will initiate or increase the rate of supply of exhaust 60 to the further processing discharge 62, and may, in some modes of operation, suspend the local discharge 61.

Figure 2A:
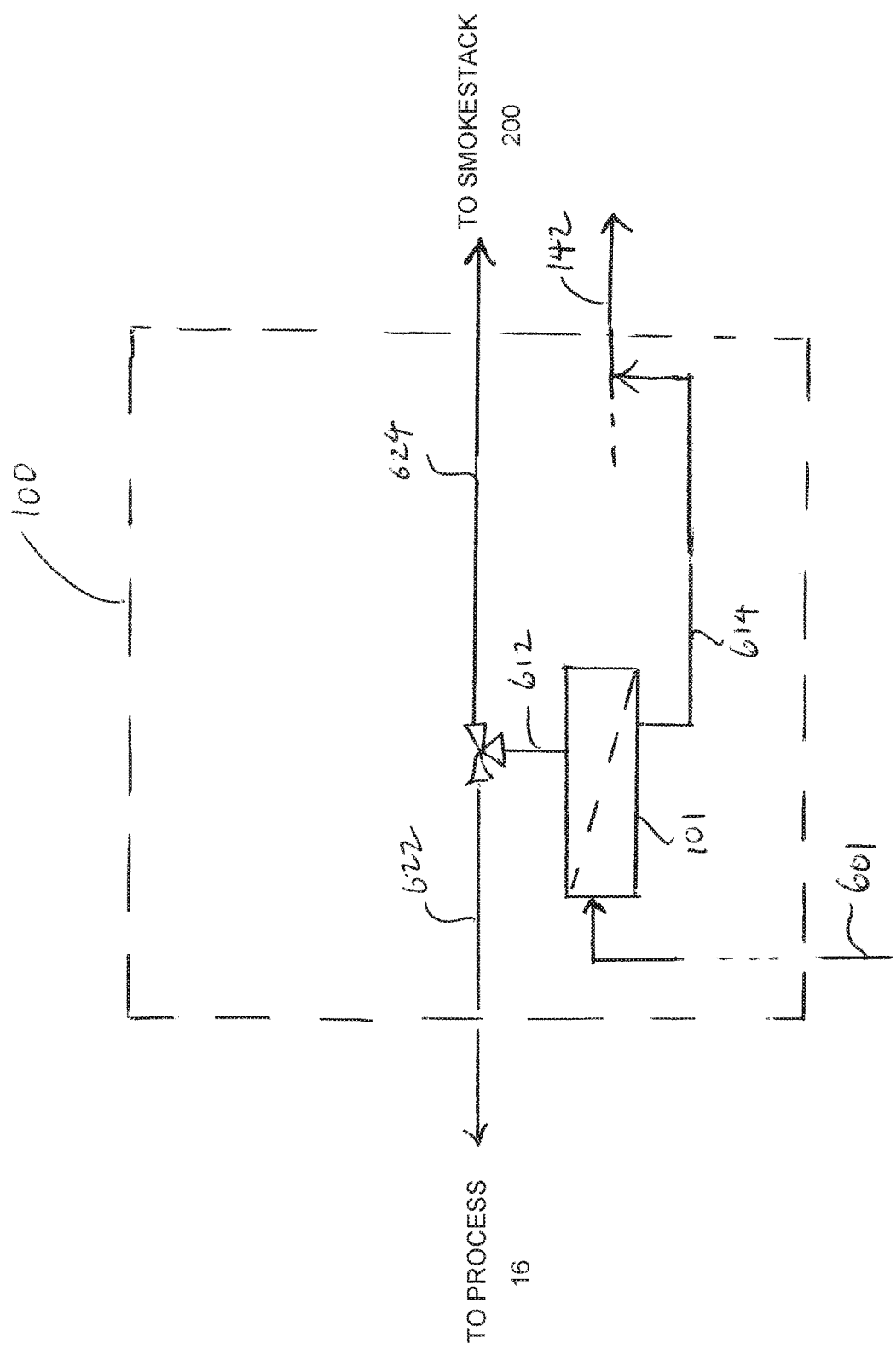
FIG. 2A is a process flow diagram of an embodiment of a subsystem embodying the gas treatment process of the process, illustrating at least a portion of the unit operations of the subsystem.
Figure 2B:
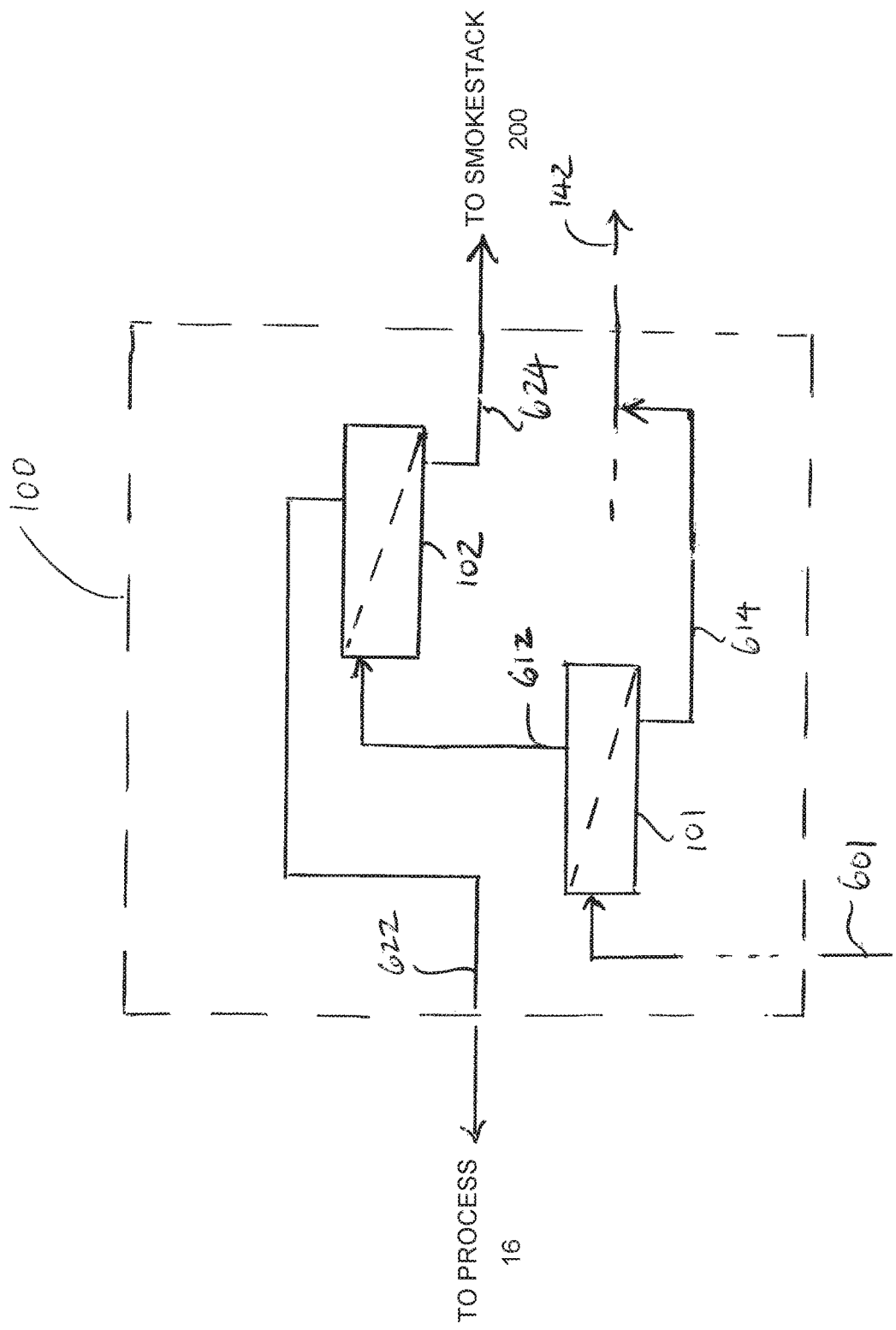
FIG. 2B is a process flow diagram of another embodiment of a subsystem embodying the gas treatment process of the process, illustrating at least a portion of the unit operations of the subsystem.

Referring to FIGS. 1, 2A and 2B, in some embodiments, for example, the gas treatment process 100 includes one or more membrane separation unit operations (or other gas separation unit operations, such as one or more gas absorbers) for effecting separation of an oxygen-rich stream from the stream 601 deriving from the exhaust 60, and delivery of a gas, of a sufficient gaseous diatomic oxygen concentration to effect combustion of a fuel, to the industrial process 16, for effecting the combustion of a fuel. In some embodiments, for example, the stream 601 is indirectly heated by at least a fraction of the gaseous exhaust material 14. The heating of the stream 601 increases the internal energy of the stream 601, including that of the oxygen-rich stream that is separated from the stream 601, such that the combustion of the fuel, effected by contacting of the oxygen-rich stream with a fuel, is enhanced by virtue of the heating of the oxygen-rich stream. As well, the indirect heating effects cooling of the carbon dioxide-comprising gaseous exhaust material 14, such that the deleterious effect on the phototrophic biomass, effected by exposure of the phototrophic biomass to high temperatures, is mitigated. In some embodiments, for example, the indirect heating is effected within a heat exchanger 900 be effecting disposition of the stream 601 in indirect heat transfer communication with the at least a fraction of the gaseous exhaust material 14.

Referring to FIG. 2A, in some embodiments, for example, the gas treatment process 100 includes a single membrane separation unit operation. 101 for effecting enrichment of gaseous diatomic oxygen. The unit operation 101 receives a stream 601 of the exhaust 60 (or a post-treatment stream that is derived from the stream 601, after the stream 601 has been subjected to pre-treatment by another unit operation within process 100) to effect separation of an oxygen-rich stream 612 and an oxygen-depleted stream 614 from the stream 601. Relative to the oxygen-depleted stream 614, the oxygen-rich stream 612 is rich in oxygen and nitrogen and any other relatively smaller molecules (e.g. mercury). Relative to the oxygen-rich stream 612, the oxygen-depleted stream 614 is rich in carbon dioxide, $NO_X$, $SO_X$, volatile organic compounds, and other relatively larger molecules. The supply of the oxygen-rich stream 612, as between the process 16 and the smokestack 200, is modulated by a valve 6003, in response to a sensed gaseous diatomic oxygen concentration within the stream 612. For a sensed gaseous diatomic oxygen concentration that is sufficient to effect combustion of fuel, the supply of the stream 612, as a stream 622, to the process 16 is initiated, or the molar rate of supply of the stream 612, as the stream 622, to the process 16 increased. For a sensed gaseous diatomic oxygen concentration that is below that which is sufficient to effect combustion of fuel, the supply of the stream 612, as a stream 624, to the smokestack 200 is initiated, or the molar rate of supply of the stream 612, as the stream 624, to the smokestack 200 is increased. The oxygen-depleted stream 614, which is rich in carbon dioxide, $NO_X$, $SO_X$, volatile organic compounds, and other relatively larger molecules, is conducted as at least a fraction of the treated material 142, and at least a fraction of the treated material 142 is supplied to the reaction zone 10. In this respect, at least a fraction of the oxygen-depleted stream 614, being rich in nutrients for encouraging growth of phototropic biomass, is supplied to the photobioreactor 12, and is depleted in gaseous diatomic oxygen, which is detrimental to growth of phototrophic biomass within the reaction zone 10. The removal of material (including gaseous diatomic oxygen) from the stream 601 also eliminates the need for larger gas handling equipment, which would have been required if the material is not removed from the steam 614 before it is recycled to the reaction zone 10 of the photobioreactor 12.

Referring to FIG. 2B, in some embodiments, for example, the gas treatment process 100 includes two membrane separation unit operations 101, 102, disposed in series for effecting a two-stage enrichment of gaseous diatomic oxygen. The unit operation 101 receives the stream 601 (or a post-treatment stream that is derived from the stream 601, after the stream 601 has been subjected to pre-treatment by another unit operation within process 100) to effect separation of an oxygen-rich stream 612 and an oxygen-depleted stream 614 from the stream 611. Relative to the oxygen-depleted stream 614, the oxygen-rich stream 612 is rich in oxygen and nitrogen and any other relatively smaller molecules (e.g. mercury). Relative to the oxygen-rich stream 612, the oxygen-depleted stream 614 is rich in carbon dioxide, $NO_X$, $SO_X$, volatile organic compounds, and other relatively larger molecules. The oxygen-rich stream 612 is supplied to the membrane separation unit operation 201 and is separated into a further oxygen-enriched stream 622 and a nitrogen-enriched stream 624. The further oxygen-enriched stream 622 is supplied to the industrial process 16, and the nitrogen-rich stream 624 is supplied to the smokestack 200. The oxygen-depleted stream 614, which is rich in carbon dioxide, $NO_X$, $SO_X$, volatile organic compounds, and other relatively larger molecules, is conducted as at least a fraction of the treated material 142, and at least a fraction of the treated material 142 is supplied to the reaction zone 10 of the photobioreactor 12. In this respect, at least a fraction of the oxygen-depleted stream 614, being rich in nutrients for encouraging growth of phototropic biomass, is supplied to the photobioreactor 12, and is depleted in gaseous diatomic oxygen, which is detrimental to growth of phototrophic biomass within the reaction zone 10. The removal of material (including gaseous diatomic oxygen) from the stream 601 also eliminates the need for larger gas handling equipment, which would have been required if the material is not removed from the steam 614 before it is recycled to the reaction zone 10 of the photobioreactor 12.

Figure 3:
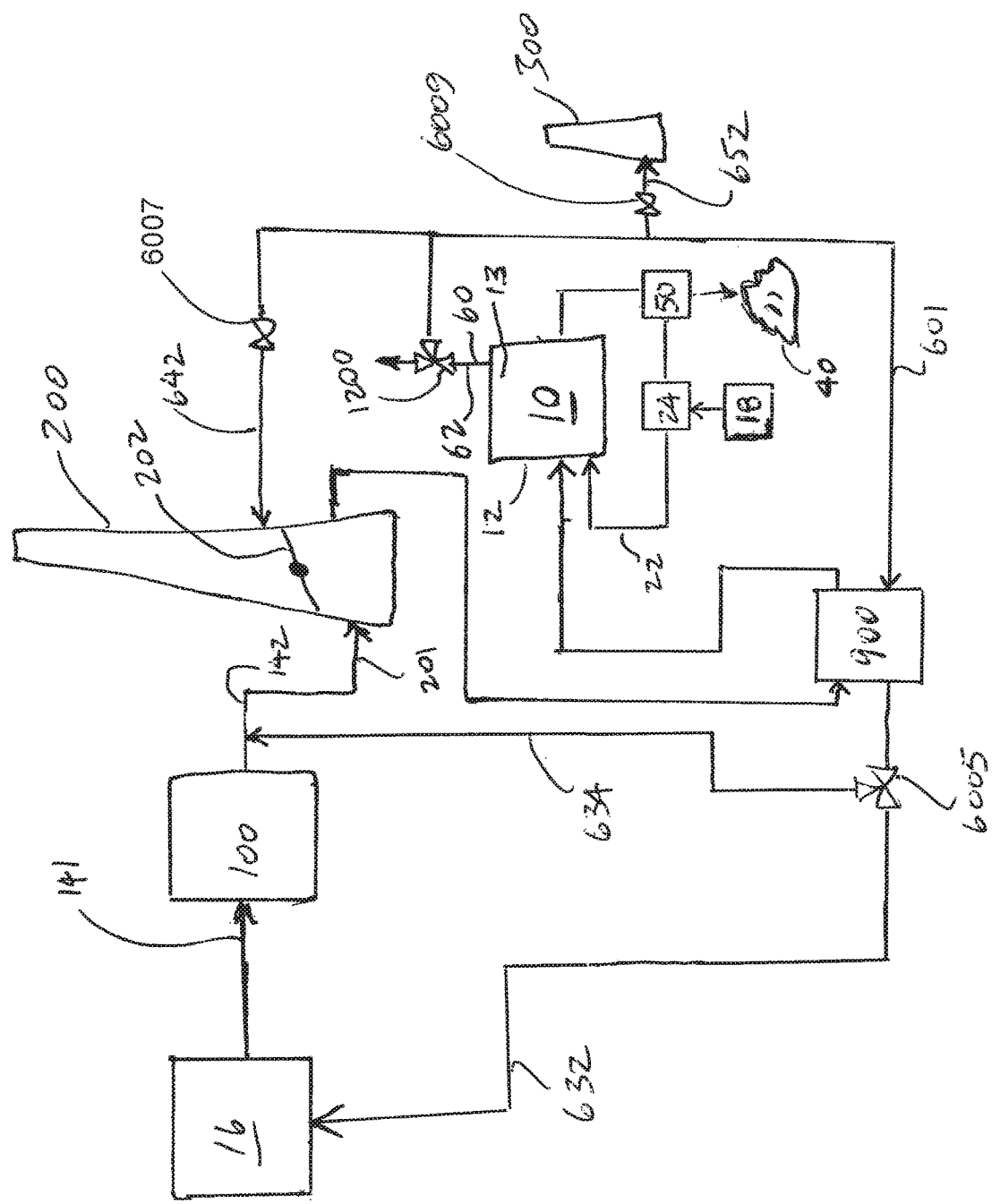
FIG. 3 is a process flow diagram of another embodiment of a system embodying the process.

Referring to FIG. 3, in some embodiments, for example, the gas treatment process 100 is not configured for effecting enrichment of gaseous diatomic oxygen, such that at least a fraction of the exhaust 60 is supplied to the process 16 in response to sensing of a concentration of gaseous diatomic oxygen that is sufficient to effect combustion of a fuel. In this respect, in some embodiments, for example, a valve 6005 is provided to modulate supply of the stream 601, as between the process 16 and as a recycle stream to the photobioreactor 10. In this respect, in response to the sensing of a gaseous diatomic oxygen concentration that is sufficient to effect combustion of a fuel, supply of the stream 601, as a stream 632, to the process 16, is initiated, or a molar rate of supply of the stream 601, as a stream 632, to the process 16, is increased. In parallel, the supply of the stream 601, as a stream 634, to the treated exhaust 142, is suspended, or the molar rate of supply of the stream 601, as a stream 634, to the treated exhaust 142, is decreased. Conversely, in response to the sensing of a gaseous diatomic oxygen concentration that is lower than that sufficient to effect combustion of a fuel, the supply of the stream 601, as a stream 632, to the process 16, is suspended, or the molar rate of supply of the stream 601, as a stream 632, to the process 16, is decreased. In parallel, the supply of the stream 601, as a stream 634, to the treated exhaust 142, is initiated, or the molar rate of supply of the stream 601, as a stream 634, to the treated exhaust 142, is increased.

Referring to FIGS. 1 and 3, in some embodiments, for example, and during upset conditions, at least a fraction of the exhaust 60 is conducted to the smokestack 200, or to a cold stack 300, so as to effect its discharge into the environment at an elevation above ground level. The smokestack 200 may be a pre-existing smokestack that had been previously receiving at least a fraction of the exhaust 14 from the process 16 prior to commissioning of the photobioreactor 12, or which is currently receiving a fraction of the exhaust 14 from the process 16, such as while a fraction of the exhaust 14 is being supplied to the photobioreactor 12 as the photobioreactor supply 122. If, however, the smokestack 200 is remote from the photobioreactor 12, a cold stack 300, local to the photobioreactor 12, may be provided to provide the same functionality as the smokestack 200, without the added infrastructure and expense of having to conduct the exhaust 60, over long distances, to a remote smokestack 200. Under normal operating conditions, the exhaust 60 is not discharged to a smokestack 200 or a cold stack 300, but is substantially retained within the system, as described above, unless the sensed concentration of the gas components being sensed are sufficiently low such that local discharge is permissible and is effected through the valve 1200. However, under upset conditions, such as when gas handling equipment fails, or when growth of the phototrophic biomass is suspended, it may not desirable to discharge at least a fraction of the exhaust 60 as the further processing discharge 62 for further downstream processing, as described above. In this situation, a valve 6007 is provided for modulating the rate of supply of at least a fraction of the discharge 62, as a stream 642, to the smokestack 200, and may become disposed to effect fluid communication between the reaction zone 10 and the smokestack 200, when upset conditions are sensed and a sensed gas concentration (for example, carbon dioxide concentration) exceeds a predetermined threshold. Similarly, a valve 6009 is provided for modulating the rate of supply of the discharge 62, as a stream 652 to the coldstack 300, and may become disposed to effect fluid communication between the reaction zone 10 and the smokestack 300, when upset conditions are sensed and a sensed gas concentration (for example, carbon dioxide concentration) exceeds a predetermined threshold.

Figure 4:
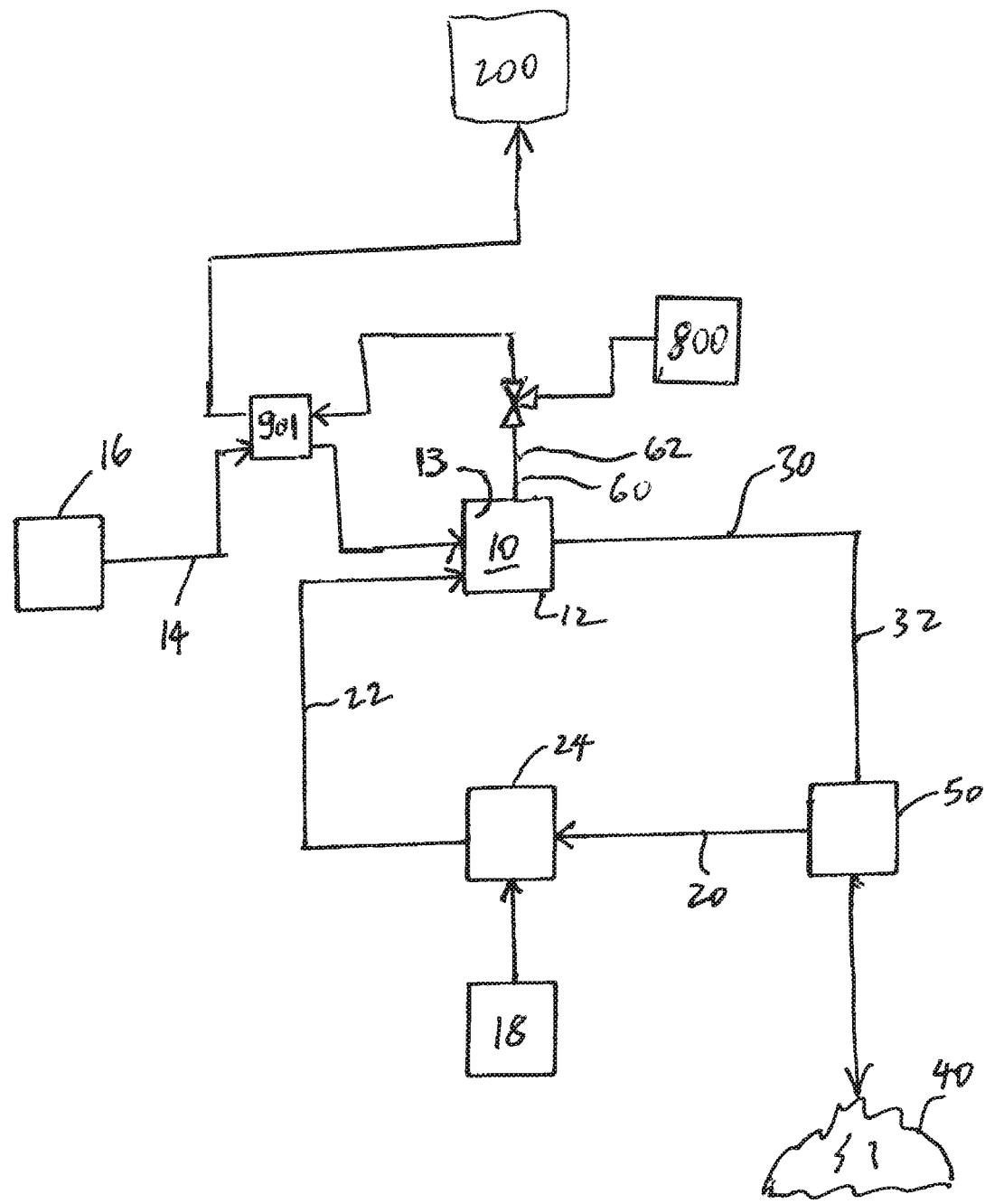
FIG. 4 is a process flow diagram of another embodiment of a system embodying the process.

Referring to FIG. 4, in some embodiments, for example, the process includes modulating distribution of a molar rate of supply of carbon dioxide, being exhausted from the photobioreactor (i.e. photobioreactor-exhausted carbon dioxide 62), as between a smokestack 200 and at least another point of discharge 800. The at least another point of discharge can include a point of discharge for supplying the exhausted carbon dioxide 62 as part of the photobioreactor exhaust 60 to any one of the reprocessing operations described above. The at least another point of discharge 800 can also be a discharge into the local environment, such as at ground level.

Modulating includes any one of: (a) initiating the supply of the photobioreactor-exhausted carbon dioxide to the smokestack 200, (b) suspending the supply of the photobioreactor-exhausted carbon dioxide to the smokestack 200, (c) increasing the molar rate of supply of the photobioreactor-exhausted carbon dioxide to the smokestack 200, or (d) decreasing the molar rate of supply of the photobioreactor-exhausted carbon dioxide to the smokestack 200. By initiating the supply of the photobioreactor-exhausted carbon dioxide to the smokestack 200, or increasing the molar rate of supply of the photobioreactor-exhausted carbon dioxide to the smokestack 200, either the supply of the photobioreactor-exhausted carbon dioxide to the at least another point of discharge is suspended, or the molar rate of supply of the photobioreactor-exhausted carbon dioxide to the at least another point of discharge is decreased. By suspending the supply of the photobioreactor-exhausted carbon dioxide to the smokestack 200, or increasing the molar rate of supply of the photobioreactor-exhausted carbon dioxide to the smokestack 200, either the supply of the photobioreactor-exhausted carbon dioxide to the at least another point of discharge is initiated, or the molar rate of supply of the photobioreactor-exhausted carbon dioxide to the at least another point of discharge is increased.

In some embodiments, for example, a fraction of the carbon dioxide-comprising exhaust material 14, being discharged by a carbon dioxide-comprising gaseous exhaust material producing process 16, is being supplied to the smokestack 200 while another fraction of the carbon dioxide-comprising exhaust material 14 is being supplied to the reaction zone 10. In this respect, the at least a fraction of carbon dioxide-comprising gaseous exhaust material 14 being supplied to the reaction zone 10 is less than the entirety, or the substantial entirety, of the carbon dioxide gaseous exhaust material 14 being discharged by the carbon dioxide-comprising gaseous exhaust material producing process 16.

In some embodiments, for example, the modulating is effected based on an indication of the molar rate at which carbon dioxide is being exhausted from the photobioreactor 12. In some embodiments, for example, the indication is a sensed indication. In some of these embodiments, for example, the sensed indication includes a sensed carbon dioxide concentration of the carbon dioxide-comprising gaseous exhaust material 14, or a sensed carbon dioxide concentration of the gaseous photobioreactor exhaust 60, or a sensed molar rate of carbon dioxide being discharged from the photobioreactor 12. The sensing of carbon dioxide concentration can be effected by a carbon dioxide sensor. The sensing of molar rate of carbon dioxide being exhausted from the photobioreactor 12 can be effected with the combination of a flow sensor and a carbon dioxide sensor.

In some embodiments, for example, the modulating is initiating the supply, or increasing the molar rate of supply, of the photobioreactor-exhausted carbon dioxide to the smokestack 200, and the modulating is effected in response to the sensing of either one of (i) an indication of a carbon dioxide concentration of the gaseous photobioreactor exhaust 60 that exceeds a predetermined concentration, or (ii) an indication of a carbon dioxide concentration of the gaseous exhaust material 14 that exceeds a predetermined concentration. The predetermined concentration being one that represents a threshold carbon dioxide concentration, above which the photobioreactor-exhausted carbon dioxide should be supplied to the smokestack 200 for purposes of environmental abatement. In this respect, a carbon dioxide sensor senses the carbon dioxide concentration and sends a signal representative of the sensed carbon dioxide concentration to a controller, the controller compares the received signal to a set point representative of the predetermined concentration, determines that the sensed carbon dioxide concentration exceeds the predetermined concentration, and transmits a signal to a flow control device 1200, disposed between the photobioreactor 12 and the smokestack 200 for selectively interfering with fluid communication between the photobioreactor 12 and the smokestack 100, to effect initiation of supply of, or an increase in the molar rate of supply of, the photobioreactor-exhausted carbon dioxide to the smokestack 200.

In some embodiments, for example the modulating is initiating the supply, or increasing the molar rate of supply, of the photobioreactor-exhausted carbon dioxide to the smokestack 200, and the modulating is effected in response to the sensing of a molar rate of discharge of carbon dioxide from the photobioreactor 12 that exceeds a predetermined molar flow rate. The predetermined molar flow rate being one that represents a threshold molar flow rate, above which the photobioreactor-exhausted carbon dioxide should be supplied to the smokestack 200 for purposes of environmental abatement. In this respect, a carbon dioxide sensor senses the carbon dioxide concentration of the discharged photobioreactor exhaust 60 and sends a signal representative of the sensed carbon dioxide concentration to a controller, and, in parallel, a flow sensor sense the molar rate of flow of photobioreactor exhaust 60 being discharged from the photobioreactor and send a signal of the sensed molar flow rate to the controller. The controller receives the signals and generates a value representative of the molar rate of carbon dioxide being discharged from the photobioreactor 12 and compares the generated value to a set point representative of a predetermined molar flow rate, determines that the generated value representative of the molar rate of carbon dioxide being discharged from the photobioreactor 12 exceeds the predetermined molar flow rate, and transmits a signal to a flow control device 1200, disposed between the photobioreactor 12 and the smokestack 200 for selectively interfering with fluid communication between the photobioreactor 12 and the smokestack 200, to effect initiation of supply of, or an increase in the molar rate of supply of, the photobioreactor-exhausted carbon dioxide to the smokestack 200.

In some embodiments, for example, the photobioreactor-exhausted carbon dioxide 62 is indirectly heated by at least a fraction of the carbon dioxide-comprising gaseous exhaust material 14 being supplied to the reaction zone 10, such that an increase in temperature to the exhausted carbon dioxide 62 is effected such that the chimney effect is enhanced within the smokestack (or cold stack 300) upon the receiving of the exhausted carbon dioxide 62. As well, the indirect heating effects cooling of the carbon dioxide-comprising gaseous exhaust material 14, such that the deleterious effect on the phototrophic biomass, effected by exposure of the phototrophic biomass to high temperatures, is mitigated. In some embodiments, for example, the indirect heating is effected within a heat exchanger 901 be effecting disposition of the exhausted carbon dioxide 62 in indirect heat transfer communication with the at least a fraction of the gaseous exhaust material 14.

In some embodiments, for example, the photobioreactor-exhausted carbon dioxide 62 is indirectly heated using low grade heat from industrial processes, or with solar radiation (such as that portion of the solar radiation which is rejected and not used for effecting photosynthesis within the reaction zone 10). This heating of the exhausted carbon dioxide effects an increase in temperature to the exhausted carbon dioxide 62 such that the chimney effect is enhanced within the smokestack (or cold stack 300) upon the receiving of the exhausted carbon dioxide 62.

The systems illustrated in FIGS. 1, 2A, 2B, 3 and 4 may include a controller and various sensors to effect desired control over the valves and, therefore, the transport or conduction of the materials. As well, various flowmetres may be provided to verify that desired fluid transport is occurring, and to identify upset conditions so as to enable execution of evasive action to prevent or mitigated inadvertent emission of gases into the local environment.

In the above description, for purposes of explanation, numerous details are set forth in order to provide a thorough understanding of the present disclosure. However, it will be apparent to one skilled in the art that these specific details are not required in order to practice the present disclosure. Although certain dimensions and materials are described for implementing the disclosed example embodiments, other suitable dimensions and/or materials may be used within the scope of this disclosure. All such modifications and variations, including all suitable current and future changes in technology, are believed to be within the sphere and scope of the present disclosure. All references mentioned are hereby incorporated by reference in their entirety.

The invention claimed is:

1. A process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, comprising:
   supplying at least a fraction of gaseous exhaust material, being discharged from an industrial process, to the reaction zone;
   exposing the reaction mixture to photosynthetically active light radiation and effecting growth of the phototrophic biomass in the reaction zone, wherein the effected growth includes growth effected by photosynthesis;
   discharging a gaseous exhaust from the reaction zone;
   separating at least an oxygen-rich product from the gaseous exhaust that is discharged from the reaction zone; and
   contacting the oxygen-rich product with a fuel to effect combustion.

2. The process of claim 1, wherein the contacting of the oxygen-rich product with a fuel is effected within a combustor of the industrial process.

3. The process of claim 2, further comprising, prior to the contacting, supplying the oxygen-rich product to the combustor.

4. The process of claim 1, wherein the separating includes separating an oxygen-depleted product from the gaseous exhaust that is discharged from the reaction zone;
   and further comprising supplying the oxygen-depleted product to the reaction zone.

5. A process for growing a phototrophic biomass in a reaction zone of a photobioreactor, wherein the reaction zone includes a reaction mixture that is operative for effecting photosynthesis upon exposure to photosynthetically active light radiation, wherein the reaction mixture includes phototrophic biomass that is operative for growth within the reaction zone, comprising:
   supplying at least a fraction of gaseous exhaust material, being discharged from an industrial process, to the reaction zone;
   exposing the reaction mixture to photosynthetically active light radiation and effecting growth of the phototrophic biomass in the reaction zone, wherein the effected growth includes growth effected by photosynthesis;
   discharging an algae-containing effluent and a gaseous exhaust from the reaction zone;
   separating at least an oxygen-depleted product from the gaseous exhaust that is discharged from the reaction zone; and
   supplying the oxygen-depleted product to the reaction zone.

6. The process of claim 5, further comprising contacting at least a fraction of the gaseous exhaust with a fuel to effect combustion of the fuel.

7. The process of claim 5, further comprising supplying at least a fraction of the gaseous exhaust to a combustor, and effecting contacting of the at least a fraction of the gaseous exhaust with a fuel to effect combustion of the fuel.

8. The process of claim 6, wherein, prior to the contacting, the gaseous exhaust is treated to effect generation of an oxygen-enriched product, wherein the at least a fraction of the gaseous exhaust includes the oxygen-enriched product.

* * * * *